United States Patent
Gao et al.

(10) Patent No.: US 11,170,504 B2
(45) Date of Patent: Nov. 9, 2021

(54) METHOD AND SYSTEM FOR INTRACEREBRAL HEMORRHAGE DETECTION AND SEGMENTATION BASED ON A MULTI-TASK FULLY CONVOLUTIONAL NETWORK

(71) Applicant: CURACLOUD CORPORATION, Seattle, WA (US)

(72) Inventors: Feng Gao, Seattle, WA (US); Youbing Yin, Kenmore, WA (US); Danfeng Guo, Beijing (CN); Pengfei Zhao, Shenzhen (CN); Xin Wang, Seattle, WA (US); Hao-Yu Yang, Seattle, WA (US); Yue Pan, Seattle, WA (US); Yi Lu, Seattle, WA (US); Junjie Bai, Seattle, WA (US); Kunlin Cao, Kenmore, WA (US); Qi Song, Seattle, WA (US); Xiuwen Yu, Redmond, WA (US)

(73) Assignee: KEYAMED NA, INC., Seattle, WA (US)

( * ) Notice: Subject to any disclaimer, the term of this patent is extended or adjusted under 35 U.S.C. 154(b) by 16 days.

(21) Appl. No.: 16/861,114

(22) Filed: Apr. 28, 2020

(65) Prior Publication Data
US 2020/0349697 A1    Nov. 5, 2020

Related U.S. Application Data

(60) Provisional application No. 62/842,482, filed on May 2, 2019.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0042* (2013.01); *A61B 5/02042* (2013.01);
(Continued)

(58) Field of Classification Search
CPC .......................... A61B 5/0042; A61B 5/02042
See application file for complete search history.

(56) References Cited

U.S. PATENT DOCUMENTS 10,650,230 B2 *   5/2020   Johnson ............... G06K 9/4628
10,691,962 B2 *   6/2020   Mei ....................... B60W 30/09
(Continued)

OTHER PUBLICATIONS

Li R, Hu B, Liu F, Liu W, Cunningham F, McManus DD, Yu H Detection of Bleeding Events in Electronic Health Record Notes Using Convolutional Neural Network Models Enhanced With Recurrent Neural Network Autoencoders: Deep Learning Approach JMIR Med Inform 2019;7(1):e10788 (Year: 2019).*
(Continued)

*Primary Examiner* — Hadi Akhavannik
(74) *Attorney, Agent, or Firm* — Bayes PLLC

(57) ABSTRACT

Embodiments of the disclosure provide systems and methods for detecting an intracerebral hemorrhage (ICH). The system includes a communication interface configured to receive a sequence of image slices and an end-to-end multi-task learning model. The sequence of image slices is the head scan images of a subject acquired by an image acquisition device. The end-to-end multi-task learning model includes an encoder, a bi-directional Convolutional Recurrent Neural Network (ConvRNN), a decoder, and a classifier. The system further includes at least one processor configured to extract feature maps from each image slice using the encoder, capture contextual information between adjacent image slices using the bi-directional ConvRNN, and detect the ICH of the subject using the classifier based on the extracted feature maps of the image slices and the
(Continued)

contextual information or segment each image slice using the decoder to obtain an ICH region based on the extracted feature maps of the image slice.

20 Claims, 8 Drawing Sheets

(51) Int. Cl.
| | | |
|---|---|---|
| *G06K 9/46* | (2006.01) | |
| *G06K 9/62* | (2006.01) | |
| *G06T 1/00* | (2006.01) | |
| *G06T 7/11* | (2017.01) | |
| *G06N 3/04* | (2006.01) | |
| *G06N 3/08* | (2006.01) | |
| *A61B 5/02* | (2006.01) | |
| *A61B 5/00* | (2006.01) | |
| *G06T 11/00* | (2006.01) | |

(52) U.S. Cl.
CPC .............. *A61B 5/7264* (2013.01); *G06K 9/46* (2013.01); *G06K 9/6267* (2013.01); *G06N 3/0445* (2013.01); *G06N 3/08* (2013.01); *G06T 1/0007* (2013.01); *G06T 7/11* (2017.01); *G06T 11/003* (2013.01); *G06T 2207/10081* (2013.01); *G06T 2207/20081* (2013.01); *G06T 2207/20084* (2013.01); *G06T 2207/30016* (2013.01); *G06T 2207/30101* (2013.01)

(56) References Cited

U.S. PATENT DOCUMENTS

| | | | |
|---|---|---|---|
| 2018/0033144 A1* | 2/2018 | Risman | G16H 30/20 |
| 2019/0139218 A1* | 5/2019 | Song | G06F 40/10 |

OTHER PUBLICATIONS

Fenglong Ma, Radha Chitta, Jing Zhou, Quanzeng You, Tong Sun, and Jing Gao. 2017. Dipole: Diagnosis Prediction in Healthcare via Attention-based Bidirectional Recurrent Neural Networks. In Proceedings of the 23rd ACM SIGKDD International Conference on Knowledge Discovery and Data Mining (KDD '17). (Year: 2017).*
Ye, H., Gao, F., Yin, Y. et al. Precise diagnosis of intracranial hemorrhage and subtypes using a three-dimensional joint convolutional and recurrent neural network. Eur Radiol 29, 6191-6201 (2019). https://doi.org/10.1007/s00330-019-06163-2 (Year: 2019).*
Arbabshirani, Mohammad R. et al., "Advanced machine learning in action: identification of intracranial hemorrhage on computed tomography scans of the head with clinical workflow integration", npj Digital Medicine (2018) 1:9; www.nature.com/npjditialmed, 7 pages.
Chilamkurthy, Sasank et al., "Development and Validation of Deep Learning Algrothims for Detection of Critical Findings in Head CT Scans," arXiv:1803.05854v2 [cs.CV] Apr. 12, 2018, 18 pages.
Heit, Jeremy J. et. al., "Imaging of Intracranial Hemmorhage", Journal of Stroke 2017:19(1):11-27, https://doi.org/10.5853/jos.2016.00563, 17 pages.
Qureshi, A. et al., "Spntaneous Intracerebral Hemorrhage", The New England Journal of Medicine, N Engl J. Med, vol. 344, No. 19, May 10, 2001, 11 pages.
Ronneberger, Olaf et al., "U-Net: Convolutional Networks for Biomedial Image Segmentation," arXiv:1505.04597v1 [cs.CV] May 18, 2015, 8 pages.

* cited by examiner

METHOD AND SYSTEM FOR INTRACEREBRAL HEMORRHAGE DETECTION AND SEGMENTATION BASED ON A MULTI-TASK FULLY CONVOLUTIONAL NETWORK

CROSS-REFERENCE TO RELATED APPLICATION

This application claims the benefit of priority to U.S. Provisional Application No. 62/842,482, filed on May 2, 2019, the entire content of which is incorporated herein by reference.

TECHNICAL FIELD

The present disclosure relates to systems and methods for intracerebral hemorrhage detection, and more particularly to, method and system for end-to-end intracerebral hemorrhage detection, segmentation and volume estimation based on a multi-task fully convolutional network.

BACKGROUND

Intracerebral hemorrhage (ICH) may lead to severe disabilities or death, though it is a common subtype of stroke. The fatality rate can be up to 40% within one month from ICH presence, and up to 54% by the end of the first year. Only 12% to 39% survivors can be long-term functionally independent after an intervention. Therefore, fast and accurate ICH diagnosis is essential for improving treatment outcomes.

ICH diagnosis mainly consists of two closely related tasks: 1) ICH detection with its subtype classification, and 2) ICH bleeding region segmentation with volume estimation. Existing ICH analysis approaches usually treat the two tasks independently by building two learning models and processing the images separately, though the two tasks may use a same set of input head scan image slices.

For example, for the ICH detection and subtype classification task, a 2D convolutional neural networks (CNN) is usually applied to each slice of a head CT scan to generate a slice-level probability score, with post-processing of the slice-level probabilities to obtain a subject-level ICH prediction. Alternatively, 3D CNN may be used to analyze a whole head CT scan to obtain a subject-level result directly. For the ICH segmentation and volume estimation task, U-Net is usually applied to segment each scan slice (e.g. 2D U-Net) or the entire head CT (e.g. 3D U-Net).

These current ICH diagnosis approaches have at least three issue. First, though ICH detection and segmentation tasks share a same set of input data, features are extracted in two separate models and not shared between the two tasks. It may decrease the algorithm performance and increase computation time in both training and prediction stages. Second, the application of 2D CNN models for ICH classification task is unable to capture contextual information along the axial axis in the head scan, while ICH classification approaches with simple 3D convolution designs have unsatisfactory performance. Third, existing approaches are designed to utilize models trained using either slice-level labels or subject-level labels, which cannot satisfy the needs in various real clinical needs.

Embodiments of the disclosure address the above problems by providing method and system for end-to-end intracerebral hemorrhage detection, segmentation and volume estimation based on a multi-task fully convolutional network.

SUMMARY

A novel deep learning-based architecture is disclosed to handle the challenging automatic intracerebral hemorrhage (ICH) detection and segmentation tasks.

In one aspect, embodiments of the disclosure provide a system for detecting an intracerebral hemorrhage. The system includes a communication interface configured to receive a sequence of image slices and an end-to-end multi-task learning model. The sequence of image slices is the head scan images of a subject and acquired by an image acquisition device. The end-to-end multi-task learning model includes an encoder, a bi-directional Convolutional Recurrent Neural Network (ConvRNN), a decoder, and a classifier. The system further includes at least one processor configured to extract feature maps from each image slice using the encoder, capture contextual information between adjacent image slices using the bi-directional ConvRNN, and detect the ICH of the subject using the classifier based on the extracted feature maps of the image slices and the contextual information or segment each image slice using the decoder to obtain an ICH region based on the extracted feature maps of the image slice.

In another aspect, embodiments of the disclosure also provide a method for detecting an intracerebral hemorrhage (ICH). The method includes receiving a sequence of image slices and an end-to-end multi-task learning model. The sequence of image slices is head scan images of a subject and acquired by an image acquisition device. The end-to-end multi-task learning model includes an encoder, a bi-directional Convolutional Recurrent Neural Network (ConvRNN), a decoder, and a classifier. The method also includes extracting, by at least one processor, feature maps from each image slice using the encoder. The method further includes capturing, by at least one processor, contextual information between adjacent image slices using the bi-directional ConvRNN. The method also includes detecting, by at least one processor, the ICH of the subject using the classifier based on the extracted feature maps of the image slices and the contextual information or segmenting, by the at least one processor, each image slice using the decoder to obtain an ICH region based on the extracted feature maps of the image slice.

In yet another aspect, embodiments of the disclosure further provide a non-transitory computer-readable medium having instructions stored thereon that, when executed by at least one processor, causes the at least one processor to perform a method for detecting an intracerebral hemorrhage (ICH). The method includes receiving a sequence of image slices and an end-to-end multi-task learning model. The sequence of image slices is head scan images of a subject and acquired by an image acquisition device. The end-to-end multi-task learning model includes an encoder, a bi-directional Convolutional Recurrent Neural Network (ConvRNN), a decoder, and a classifier. The method also includes extracting, by at least one processor, feature maps from each image slice using the encoder. The method further includes capturing, by at least one processor, contextual information between adjacent image slices using the bi-directional ConvRNN. The method also includes detecting, by at least one processor, the ICH of the subject using the classifier based on the extracted feature maps of the image slices and the contextual information or segmenting each image slice using the decoder to obtain an ICH region based on the extracted feature maps of the image slice.

It is to be understood that both the foregoing general description and the following detailed description are exemplary and explanatory only and are not restrictive of the invention, as claimed.

DETAILED DESCRIPTION

Reference will now be made in detail to the exemplary embodiments, examples of which are illustrated in the accompanying drawings.

The disclosed systems and methods use an end-to-end multi-task learning model for modeling head scan images to solve ICH detection and segmentation problems. In some embodiments, this end-to-end multi-task learning model may include the following modules: an encoder, a decoder, a bi-directional Convolutional Recurrent Neural Network (ConvRNN), a classification, and an optional attention module. In some embodiments, the encoder module extracts task-relevant features from the scan slices, which is used by the ConvRNN module and the decoder module as an input. The decoder module combines features of different granularities to generate segmentation results and estimation of bleeding volume as the output of the end-to-end multi-task learning model. In some embodiments, the ConvRNN module captures context information between adjacent slides without losing spatial information encoded in the slice-level feature maps. The classification module then utilizes the output feature maps from the ConvRNN module to generate slice-level and subject-level classification results. In some embodiments, the end-to-end multi-task learning model may optionally include an attention model to magnify signals from salient features and filter out task-irrelevant features.

The disclosed systems and methods provide several improvements over conventional approaches. First, the learning model can perform ICH detection and segmentation tasks simultaneously. This enables information sharing and complementation between the two different but closely related tasks. Modules of the learning model are jointly optimized, which can preserve the overall performance of the two tasks while reducing time consumption in both training and prediction stages. Second, the model can seamlessly combine the advantages of Convolutional Neural Network (CNN) on image feature extraction and that of ConvRNN on sequential learning of spatial information. Model performance can be further improved by using the combined 2D and 3D information extracted from slice-level and subject-level images. Third, the model can be flexible on the type of ICH classification labels it predicts and supports different training scenarios.

Figure 1:
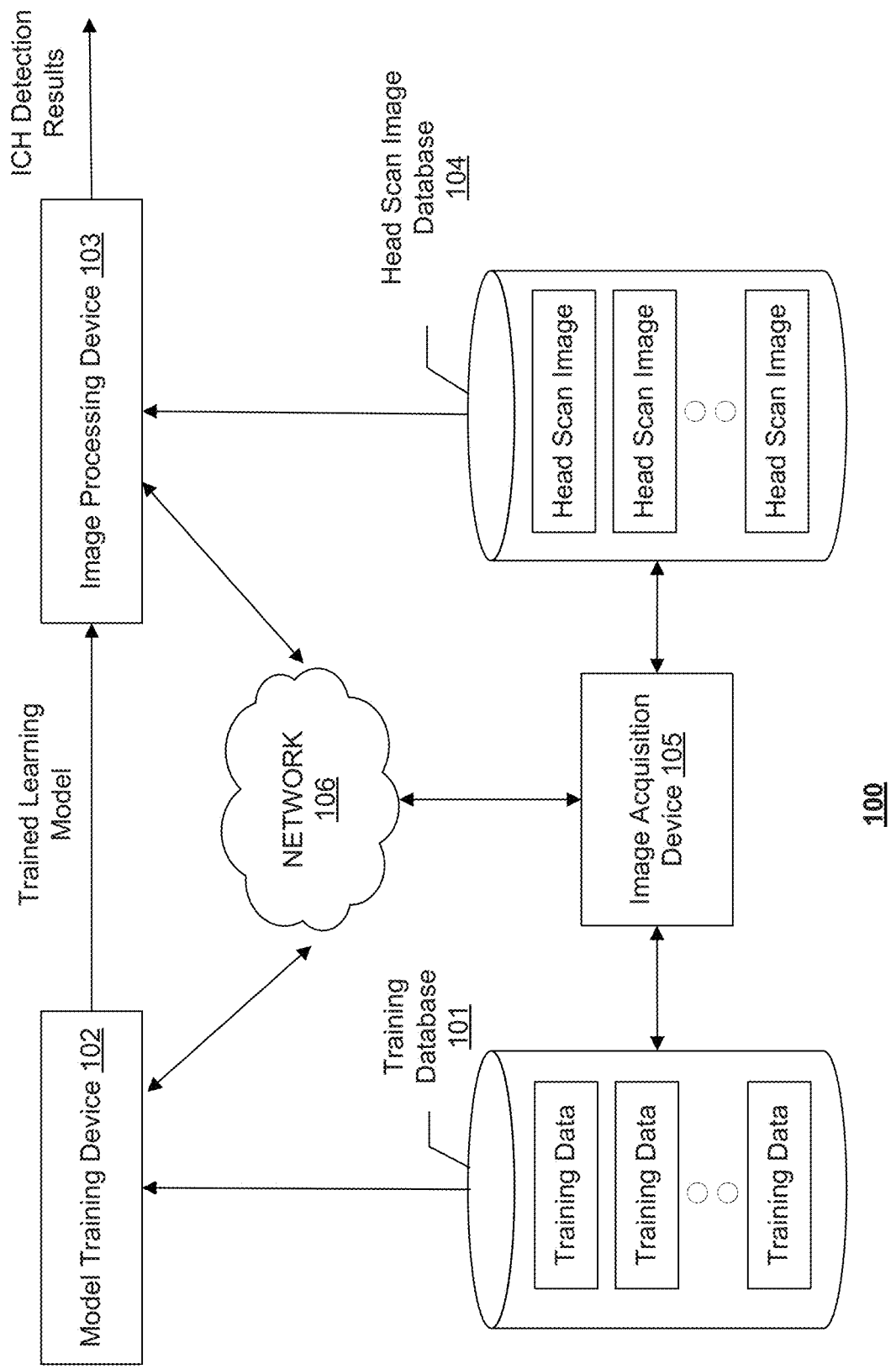
FIG. 1 illustrates a schematic diagram of an exemplary ICH detection system, according to embodiments of the disclosure.

FIG. 1 illustrates an exemplary ICH detection system 100, according to some embodiments of the present disclosure. Consistent with the present disclosure, ICH detection system 100 is configured to classify and segment biomedical images acquired by an image acquisition device 105. In some embodiments, the biomedical images may be head scan image that can be used to diagnose ICH. In some embodiments, image acquisition device 105 may be using one or more imaging modalities that are suitable for head scans, including, e.g., Magnetic Resonance Imaging (MRI), Computed Tomography (CT), functional MRI (e.g., fMRI, DCE-MRI and diffusion MRI), Cone Beam CT (CBCT), Positron Emission Tomography (PET), Single-Photon Emission Computed Tomography (SPECT), etc. In some embodiments, the biomedical image captured may be two dimensional (2D) or three dimensional (3D) images. A 3D image may contain multiple 2D image slices.

As shown in FIG. 1, ICH detection system 100 may include components for performing two phases, a training phase and a prediction phase. To perform the training phase, ICH detection system 100 may include a training database 101 and a model training device 102. To perform the prediction phase, ICH detection system 100 may include an image processing device 103 and a biomedical image database 104. In some embodiments, ICH detection system 100 may include more or less of the components shown in FIG. 1. For example, when a learning model for classifying and segmenting the images is pre-trained and provided, ICH detection system 100 may include only image processing device 103 and head scan image database 104.

ICH detection system 100 may optionally include a network 106 to facilitate the communication among the various components of ICH detection system 100, such as databases 101 and 104, devices 102, 103, and 105. For example, network 106 may be a local area network (LAN), a wireless network, a cloud computing environment (e.g., software as a service, platform as a service, infrastructure as a service), a client-server, a wide area network (WAN), etc. In some embodiments, network 106 may be replaced by wired data communication systems or devices.

In some embodiments, the various components of ICH detection system 100 may be remote from each other or in different locations, and be connected through network 106 as shown in FIG. 1. In some alternative embodiments, certain components of ICH detection system 100 may be located on the same site or inside one device. For example, training database 101 may be located on-site with or be part of model training device 102. As another example, model training device 102 and image processing device 103 may be inside the same computer or processing device.

Model training device 102 may use the training data received from training database 101 to train a learning model for classifying and segmenting the sequence of image slices received from, e.g., head scan image database 104. As shown in FIG. 1, model training device 102 may communicate with training database 101 to receive one or more sets of training data. Each set of training data may include head scan images (2D or 3D)s from a subject and the corresponding ground truth ICH labels and segmentation masks that provides the classification and segmentation result to each image.

Based on a bleeding location in a brain, ICH can be further categorized into 5 subtypes: epidural hemorrhage (EDH), subdural hemorrhage (SDH), subarachnoid hemorrhage (SAH), cerebral parenchymal hemorrhage (CPH) and intraventricular hemorrhage (IVH). In some embodiments, ICH subtype labels on slice-level or subject-level may be included in training data.

In some embodiments, the ground truth data may further include a set of segmentation masks of the bleeding region. The training images are previously segmented or annotated by expert operators with each pixel/voxel classified and labeled, e.g., with value 1 if the pixel/voxel indicates a bleeding or value 0 if otherwise. In some embodiments, instead of binary values, the ground truth data may be probability maps where each pixel/voxel is associated with a probability value indicating how likely the pixel/voxel indicate a bleeding. The aim of the training phase is to learn a mapping between a sequence of head scan image slices and the ground truth labels with classification and segmentation masks by finding the best fit between predictions and ground truth values over the sets of training data.

In some embodiments, the training phase may be performed "online" or "offline." An "online" training refers to performing the training phase contemporarily with the prediction phase, e.g., learning the model in real-time just prior to classifying and segmenting a biomedical image. An "online" training may have the benefit to obtain a most updated learning model based on the training data that is then available. However, an "online" training may be computational costive to perform and may not always be possible if the training data is large and/or the model is complicate. Consistent with the present disclosure, an "offline" training is used where the training phase is performed separately from the prediction phase. The learned model trained offline is saved and reused for classifying and segmenting images.

Model training device 102 may be implemented with hardware specially programmed by software that performs the training process. For example, model training device 102 may include a processor and a non-transitory computer-readable medium (discussed in detail in connection with FIG. 3). The processor may conduct the training by performing instructions of a training process stored in the computer-readable medium. Model training device 102 may additionally include input and output interfaces to communicate with training database 101, network 106, and/or a user interface (not shown). The user interface may be used for selecting sets of training data, adjusting one or more parameters of the training process, selecting or modifying a framework of the learning model, and/or manually or semi-automatically providing prediction results associated with a sequence of images for training.

Consistent with some embodiments, the end-to-end multi-task learning model may be a fully convolutional network (FCN) that include an encoder module, a decoder module, a bi-directional ConvRNN module, a classification module and an optional attention module (discussed in detail in connection with FIG. 2). However, it is contemplated that the model may include more or less modules and the structure of the model is not limited to what is disclosed as long as the model performs multiple tasks simultaneously and utilizes contextual information between adjacent image slices.

The trained learning model may be used by image processing device 103 to detect ICH in new head scan images (images that are not associated with ground-truth detection results). Image processing device 103 may receive a trained learning model, e.g., end-to-end multi-task learning model 200, from model training device 102. Image processing device 103 may include a processor and a non-transitory computer-readable medium (discussed in detail in connection with FIG. 3). The processor may perform instructions of a sequence of image slices classification and segmentation process stored in the medium. Image processing device 103 may additionally include input and output interfaces (discussed in detail in connection with FIG. 3) to communicate with head scan image database 104, network 106, and/or a user interface (not shown). The user interface may be used for selecting one or more head scan images of a subject for classification and segmentation, initiating the classification and segmentation process, displaying the head scan image and/or the classification and segmentation results.

Types of ICH detection results that the learning model may provide depend on the types of ground truth ICH labels used in a model training. In some embodiments, given a trained model $\psi$ and a sequence of input image scan $x=(x_1, x_2, \ldots, x_n)$, the model returns $\hat{y}=\psi(x)$. For example, if only slice-level binary labels (whether ICH exists or not in each training image slice) and segmentation masks are provided in the model training, the model returns $\hat{y}=(\hat{y}_{sli-b}, \hat{y}_{seg}, \hat{y}_{sub-b}, \hat{y}_v)$. If only subject-level ICH subtype labels are available in the model training, the model returns $\hat{y}=(\hat{y}_{sli-b}, \hat{y}_{seg}, \hat{y}_{sub-b}, \hat{y}_{sub-m}, \hat{y}_v)$. If only slice-level ICH subtype labels are used in the model training, the model returns $\hat{y}=(\hat{y}_{sli-b}, \hat{y}_{sli-m}, \hat{y}_{seg}, \hat{y}_{sub-b}, \hat{y}_{sub-m}, \hat{y}_v)$, where $\hat{y}_{seg}$ is the predicted segmentation, $\hat{y}_{sli-b}$ is the ICH predictions for all slices, $\hat{y}_{sli-m}$ is the subtype predictions for all slices, $\hat{y}_{sub-b}$ is the subject-level ICH prediction, $\hat{y}_{sub-m}$ is the subject-level subtype prediction, and $\hat{y}_v$ is the ICH volume estimation.

In some embodiments, the segmentation mask can include but not limited to the following examples: 1) binary ICH masks; 2) detailed ICH subtype masks; 3) ICH or subtype masks together with other desired labels such as skulls, normal brain tissues and regions outside the brain.

Image processing device 103 may communicate with head scan image database 104 to receive one or more head scan images. In some embodiments, the images stored in head scan image database 104 may include 2D image slices from a 3D scan. The images may be acquired by image acquisition devices 105. Image processing device 103 uses the trained learning model received from model training device 102 to perform one or more of: (1) predict whether ICH exists, (2) predict the subtype of ICH, and (3) determine segmentation masks of the image optionally with an estimated bleeding volume.

Figure 2:
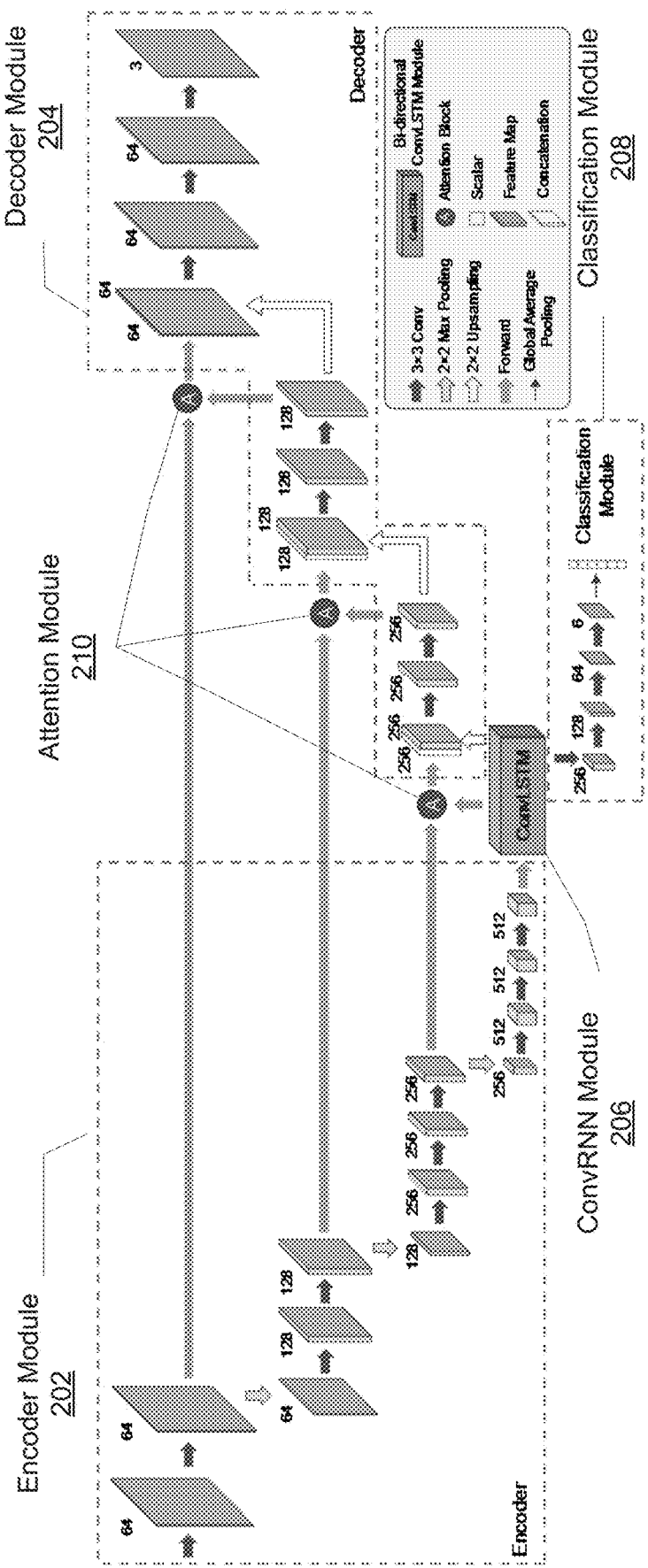
FIG. 2 illustrates an exemplary end-to-end multi-task learning model, according to embodiments of the disclosure.

FIG. 2 illustrates an exemplary end-to-end multi-task learning model 200 (hereafter, "learning model 200"), according to embodiments of the disclosure. For example, learning model 200 can be a Fully Convolutional Network (FCN). In some embodiments, learning model 200 may include an encoder module 202, a decoder module 204, a ConvRNN module 206, a classification module 208, and optionally an attention module 210. As shown in FIG. 2, encoder module 202 may include a sequence of convolution/pooling layers to extract task-relevant features from the image slices, e.g., head CT scan slices. Decoder module 204 is used to combine feature maps of different granularities to generate segmentation masks. Bi-directional ConvRNN module 206 is used to utilize the contextual information between adjacent slices to improve the slice-level feature maps. Classification module 208 utilizes output feature maps from ConvRNN module 206 to generate slice-level or subject-level ICH predictions. Attention module 210 is an optional component to magnify signals from salient features and filter out task-irrelevant features.

In some embodiments, encoder module 202 may be in any suitable convolutional neutral network (CNN) architecture, including but not limited to the CNN component of commonly used image classification architectures such as VGG, ResNet, and DenseNet. In FIG. 2, encoder module 202 employs a VGG architectures as an example to illustrate a feature map extraction procedure. For example, convolutional layers use multiple 3×3 kernel-sized filters and pooling layers use 2×2 size filters. It is contemplated that classification architectures other than VGG can be used.

Consistent with the present disclosure, ConvRNN module 206 may be used to learn contextual information between adjacent image slices across axial axis and enhance the quality of feature maps generated from encoder module 202. For example, ConvRNN module 206 may be implemented by either bidirectional Convolutional Long Short-Term Memory (ConvLSTM) or bidirectional Convolutional Gated Recurrent Unit (ConvGRU). "Adjacent image slices" refer to every two image slices immediately next to each other in the sequence of image slices. Most of the structural information captured by the adjacent image slices can be common, while the differences between the image slices could provide valuable information of bleeding or other abrupt changes. Therefore, contextual information captured by ConvRNN module 206 could assist the detection and segmentation of the bleeding regions.

Feature maps generated from ConvRNN module 206 may be fed to classification module 208 to generate slice-level or subject-level ICH detection results. In some embodiments, classification module 208 may be composed of convolution and pooling layers. For example, convolutional layers may use multiple 3×3 kernel-sized filters and pooling layers may use 2×2 size filters as shown in FIG. 2. Slice-level ICH detection predicts whether ICH exists on each input image slice (discussed in detail in connection with FIG. 4). In some embodiments, slice-level feature maps are fused to obtain subject-level feature maps using operations e.g., average/max pooling (discussed in detail in connection with FIG. 5).

Feature maps generated from ConvRNN module 206 are also used by decoder module 204 to produce segmentation masks. In some embodiments, upsampling via deconvolution is used to determine a segmentation map having the same size as the input image slice. FIG. 2 illustrates how decoder module 204 generates a segmentation map by fusing features of different granularities. For example, the output from ConvRNN module 206 is first 2× upsampled and then fused with feature maps from encoder module 202 that has the same granularity. The fusion operation can improve segmentation performance.

Figure 6:
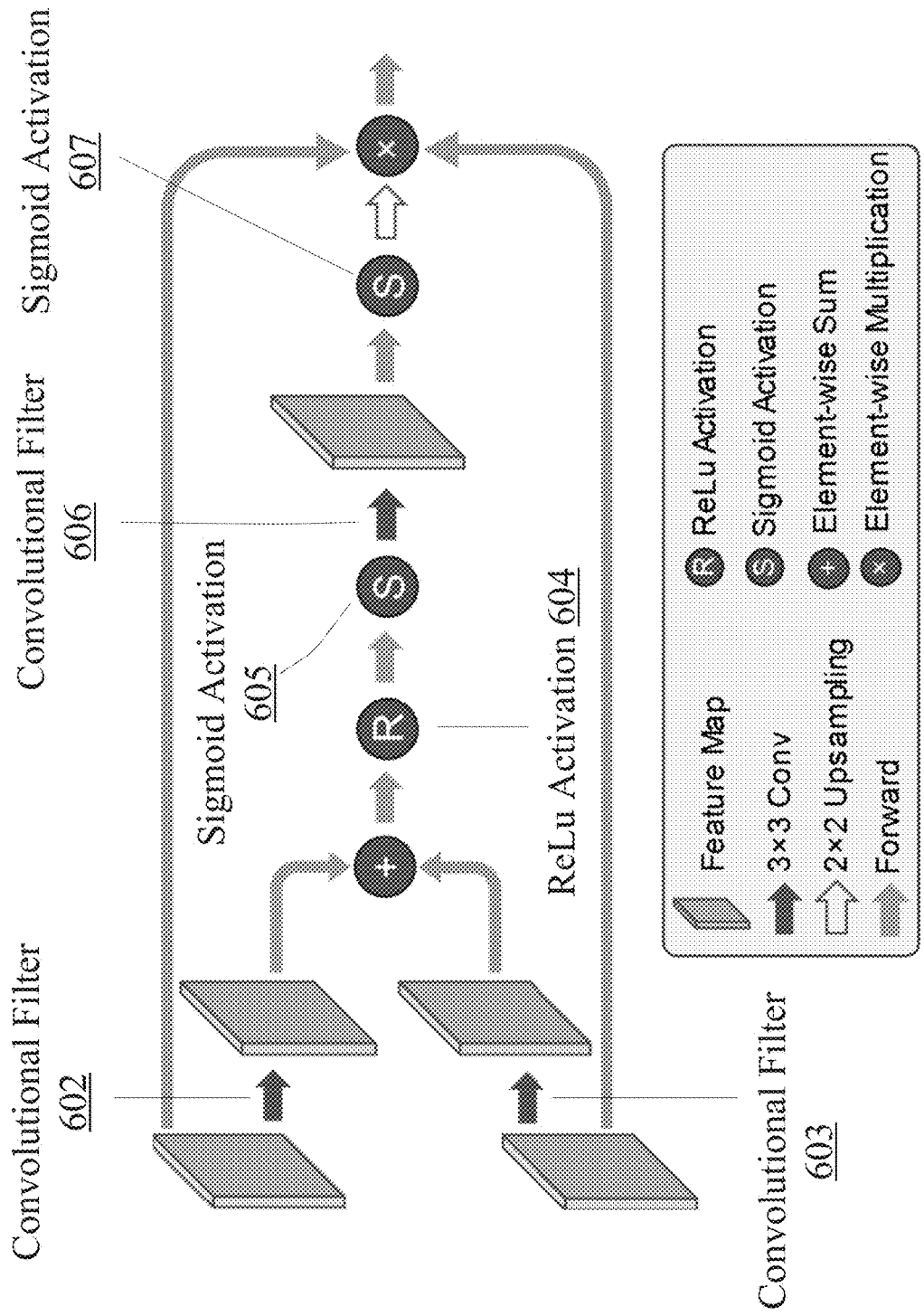
FIG. 6 is a flow diagram of an exemplary attention module, according to embodiments of the disclosure.

In some embodiments, attention module 210 can be used to enhance feature maps before a fusion operation. FIG. 6 is a flow diagram of an exemplary attention module 600, according to embodiments of the disclosure. As shown in FIG. 6, convolutional filter 602 and convolutional filter 603 are first applied to two feature maps, respectively. Convolutional filter 602 and convolutional filter 603 can be any suitable filters of any suitable sizes. For example, 3×3 kernel-sized filters are illustrated in FIG. 6. The results are then element-wise summed. ReLu activation 604 and Sigmoid activation 605 are sequentially applied to the summed feature map. The resulted feature map is downsampled using convolutional filter 606. Sigmoid activation 607 is used to determine attention weights from the downsampled feature map. The attention weight map is upsampled, e.g., using 2×2 filters, and then element-wise multiplied with the input feature maps to obtain an enhanced feature map. FIG. 6 shows one possible implementation of attention module 210. However, it is contemplated that the module can be implemented using any architectures, operations, and activations (e.g., tan h activation function) as long as it can effectively enhance feature maps.

Consistent with the present disclosure, returning to FIG. 1, model training device 102 may jointly train encoder module 202, decoder module 204, ConvRNN module 206, classification module 208, and attention module 210, using the training data from training database 101. In other words, the end-to-end multi-task learning model is trained as one model rather than different modules separately. As information propagates among the nodes in the ConvRNN module during the joint training, the jointly trained learning model can utilize information of the adjacent image slices of the subject to provide a better prediction.

As used herein, "training" an end-to-end multi-task learning model refers to determining one or more parameters of at least one layer in the network. For example, a convolution layer of encoder module 202 or decoder module 204 may include at least one filter or kernel. One or more parameters, such as kernel weights, size, shape, and structure, of the at least one filter may be determined by e.g., a backpropagation-based training process. The end-to-end multi-task learning model may be trained using supervised learning, semi-supervised learning, or unsupervised learning.

In some embodiments, a joint loss function may be used by the joint training to account for losses associated with the various tasks performed by learning model 200. In some embodiments, the losses of the various tasks may be weighted according their significance or another predetermined priority. For example, returning to FIG. 2, a loss function may be defined as $$\mathcal{L} = \lambda_{sli-b} \mathcal{L}_{sli-b} + \lambda_{sub-b} \mathcal{L}_{sub-b} + \lambda_{sli-m} \mathcal{L}_{sli-m} + \lambda_{sub-m} \mathcal{L}_{sub-m} + \lambda_{seg} \mathcal{L}_{seg} + \lambda_{v} \mathcal{L}_{v} + \rho_1 \|\psi\|_1 + \rho_2 \|\psi\|_2,$$

where parameter $\{\lambda.\}$ controls the weights of different subtask loss functions contributed in the total loss $\mathcal{L}$. Among them, $\mathcal{L}_{sli-b}$ denotes a slice-level binary classification loss, $\mathcal{L}_{sub-b}$ denotes a subject-level binary classification loss, $\mathcal{L}_{sli-m}$ denotes a slice-level ICH subtype classification loss, and $\mathcal{L}_{sub-m}$ denotes a subject-level ICH subtype classification loss. In some embodiments, $\mathcal{L}_{sli-b}$, $\mathcal{L}_{sub-b}$, $\mathcal{L}_{sli-m}$, and $\mathcal{L}_{sub-m}$ can be binary cross entropy (BCE) loss or any other suitable types of losses. In some embodiments, if ground truth of the slice-level or subject-level ICH subtype is not provided in the training database, parameters $\lambda_{sli-m}$ or $\lambda_{sub-m}$ can be set to 0. $\mathcal{L}_{seg}$ denotes a segmentation loss, which can be a soft dice loss, a cross entropy, or any other suitable types of losses. $\mathcal{L}_v$ denotes an ICH volume estimation loss and it can be a quadratic loss or any other suitable types of losses. $\|\psi\|_1$ and $\|\psi\|_2$ are $L_1/L_2$ norm of all model parameters to control the model complexity. $\{\rho.\}$ may be used to control the strength of $L_1/L_2$ regularizations. The parameters $\{\lambda., \rho.\}$ can be pre-defined or optimized together with other model parameters during training.

In some embodiments, the loss function can be optimized by using neural network optimizers such as Stochastic Gradient Descent (SGD), AdaGrad, or Adam. Backpropagation can be used to compute gradients and optimize parameters.

When applied by image processing device 103, some or all the modules of learning model 200 may be used. For example, learning model 200 may be employed to do only ICH detection (using encoder module 202, ConvRNN module 206, and classification module 208), only segmentation (using encoder module 202, ConvRNN module 206, and decoder module 204), or ICH detection and segmentation simultaneously (using all the modules of learning model 200). When performing detection and segmentation at the same time, learning model 200 can improve performance and reduce computation time. On the other hand, learning model 200 still preserves the flexibility of doing these tasks separately by only including a subset of modules.

Figure 3:
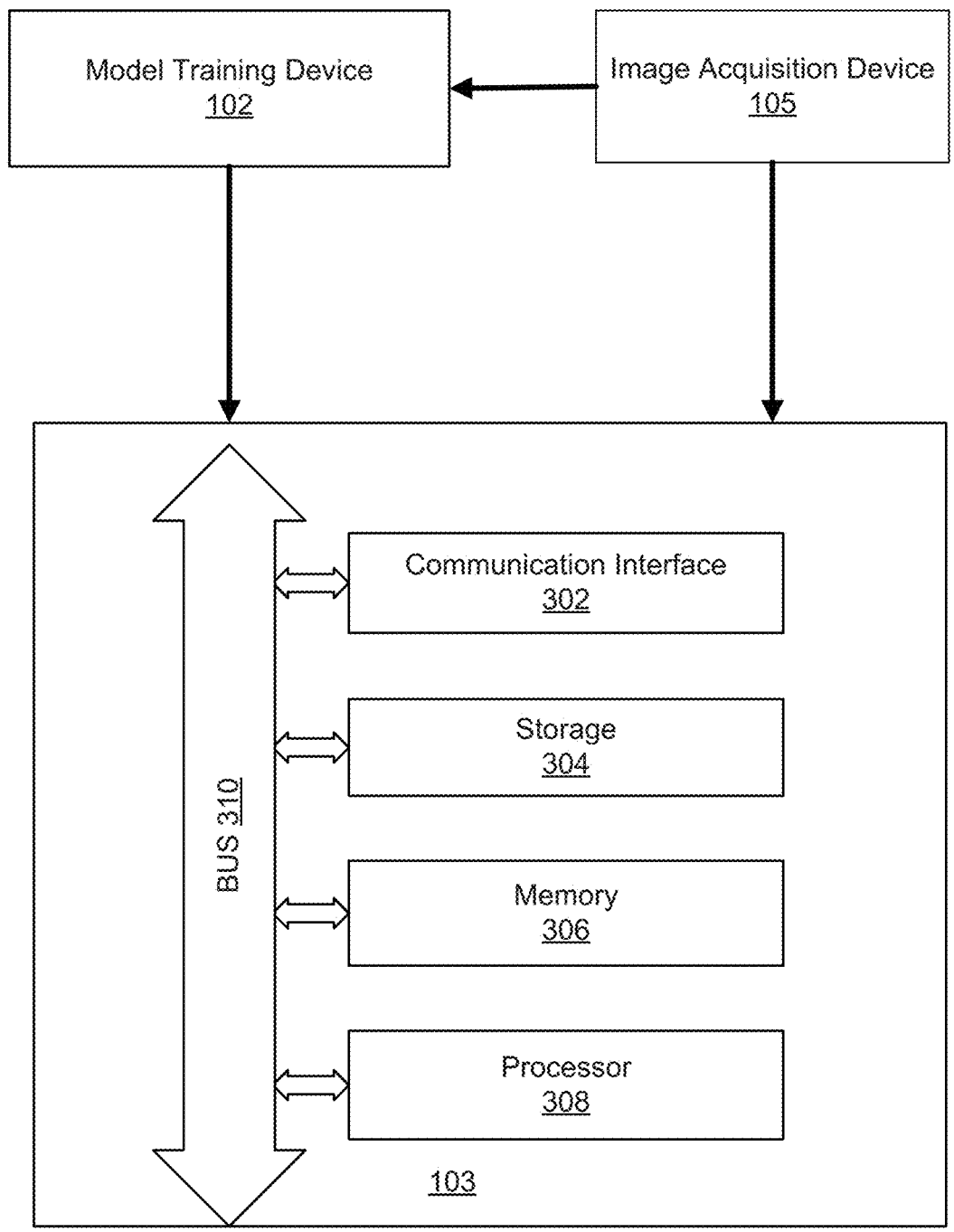
FIG. 3 illustrates a block diagram of an exemplary image processing device, according to embodiments of the disclosure.

FIG. 3 illustrates an exemplary image processing device 103, according to some embodiments of the present disclosure. In some embodiments, image processing device 103 may be a special-purpose computer, or a general-purpose computer. For example, image processing device 103 may be a computer custom-built for hospitals to perform image acquisition and image processing tasks, or a server placed in the cloud. As shown in FIG. 3, image processing device 103 may include a communication interface 302, a storage 304, a memory 306, a processor 308, and a bus 310. Communication interface 302, storage 304, memory 306, and processor 308 are connected with bus 310 and communicate with each other through bus 310.

Communication interface 302 may include a network adaptor, a cable connector, a serial connector, a USB connector, a parallel connector, a high-speed data transmission adaptor, such as fiber, USB 3.0, thunderbolt, and the like, a wireless network adaptor, such as a WiFi adaptor, a telecommunication (3G, 4G/LTE and the like) adaptor, etc. Image processing device 103 may be connected to other components of ICH detection system 100 and network 106 through communication interface 302. In some embodiments, communication interface 302 receives biomedical images (each including a sequence of image slices) from image acquisition device 105. In some embodiments, communication interface 302 also receives the trained learning model, e.g., end-to-end multi-task learning model 200, from modeling training device 102.

Storage 304/memory 306 may be a non-transitory computer-readable medium, such as a read-only memory (ROM), a random access memory (RAM), a phase-change random access memory (PRAM), a static random access memory (SRAM), a dynamic random access memory (DRAM), an electrically erasable programmable read-only memory (EEPROM), other types of random access memories (RAMs), a flash disk or other forms of flash memory, a cache, a register, a static memory, a compact disc read-only memory (CD-ROM), a digital versatile disc (DVD) or other optical storage, a cassette tape or other magnetic storage devices, or any other non-transitory medium that may be used to store information or instructions capable of being accessed by a computer device, etc.

In some embodiments, storage 304 may store the trained learning model, e.g., end-to-end multi-task learning model 200, and data, such as feature maps generated while executing the computer programs, etc. In some embodiments, memory 306 may store computer-executable instructions, such as one or more image processing programs. In some embodiments, feature maps may be extracted at different granularities from image slices stored in storage 304. The feature maps may be read from storage 304 one by one or simultaneously and stored in memory 306.

Processor 308 may be a processing device that includes one or more general processing devices, such as a microprocessor, a central processing unit (CPU), a graphics processing unit (GPU), and the like. More specifically, the processor may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The processor may also be one or more dedicated processing devices such as application specific integrated circuits (ASICs), field programmable gate arrays (FPGAs), digital signal processors (DSPs), system-on-chip (SoCs), and the like. Processor 308 may be communicatively coupled to memory 306 and configured to execute the computer-executable instructions stored thereon.

Figure 4:
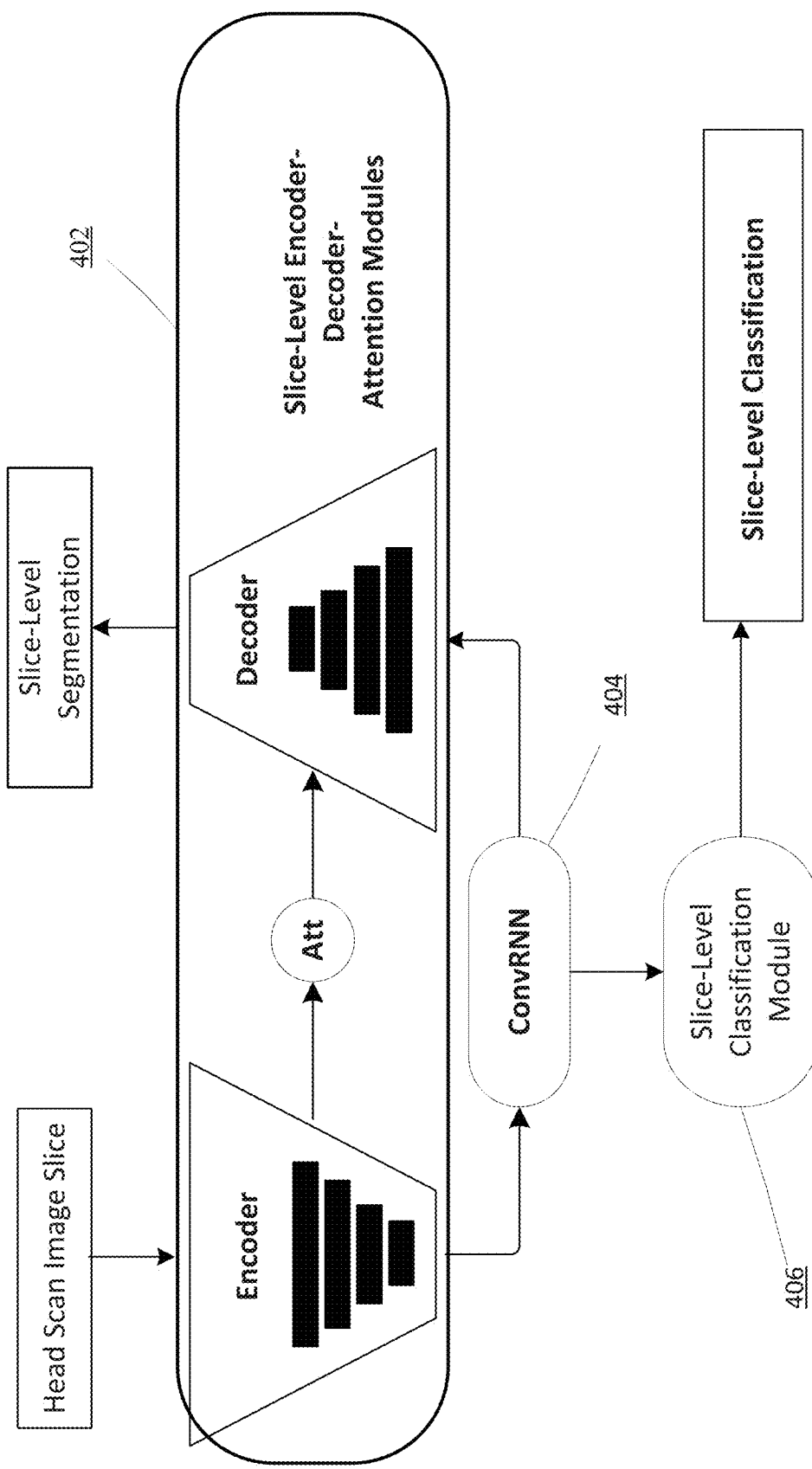
FIG. 4 is a flow diagram of an exemplary method for slice-level ICH detection and segmentation, according to embodiments of the disclosure.

In some embodiments, processor 308 is configured to detect an ICH (optionally including its subtype) or segment the images, or both. For example, as shown in FIG. 4, processor 308 may first receive an image (including the sequence of image slices) from image acquisition device 105. Processor 308 then uses the trained learning model, such as end-to-end multi-task learning model 200, to predict whether ICH exists in the received image and outputs a segmentation mask of the image. The trained learning model may include slice-level encoder-decoder-attention modules 402 (e.g., including encoder module 202, decoder module 204, and attention module 210), a ConvRNN module 404 (e.g., ConvRNN module 206), and a slice-level classification module 406 (e.g., classification module 208).

Consistent with some embodiments, processor 308 may apply the learning model to the image to perform the slice-level classification (e.g., using the slice-level classification module) and segmentation (e.g., using the decoder module) in parallel. For example, processor 308 may execute the encoder module to extract feature maps from the received image. The feature maps may then be fed to the ConvRNN module and the attention module in parallel. The ConvRNN module encodes contextual information into the feature maps, which is provided to the slice-level classification module. In some embodiments, processor 308 may additionally execute the attention module to enhance the feature maps before they are used for segmentation in the decoder module. Processor 308 may execute the slice-level classification module to generate a slice-level classification result. In some embodiments, this classification result can be either an ICH identification result or an ICH subtype label depending on the ground truth label types used in the model training.

In parallel, the decoder module produces the segmentation mask using the enhanced maps. In some embodiments, the decoder module may produce a probability map indicating the probability each pixel in the image slice belongs to a bleeding region. Processor 308 may then perform a thresholding to obtain a segmentation mask. For example, processor 308 may set pixels with probabilities above 0.8 as 1 (i.e., belong to a bleeding region) and the remaining pixels as 0 (i.e., not belong to a bleeding region). The threshold may be set by an operator or automatically selected by processor 308.

Figure 5:
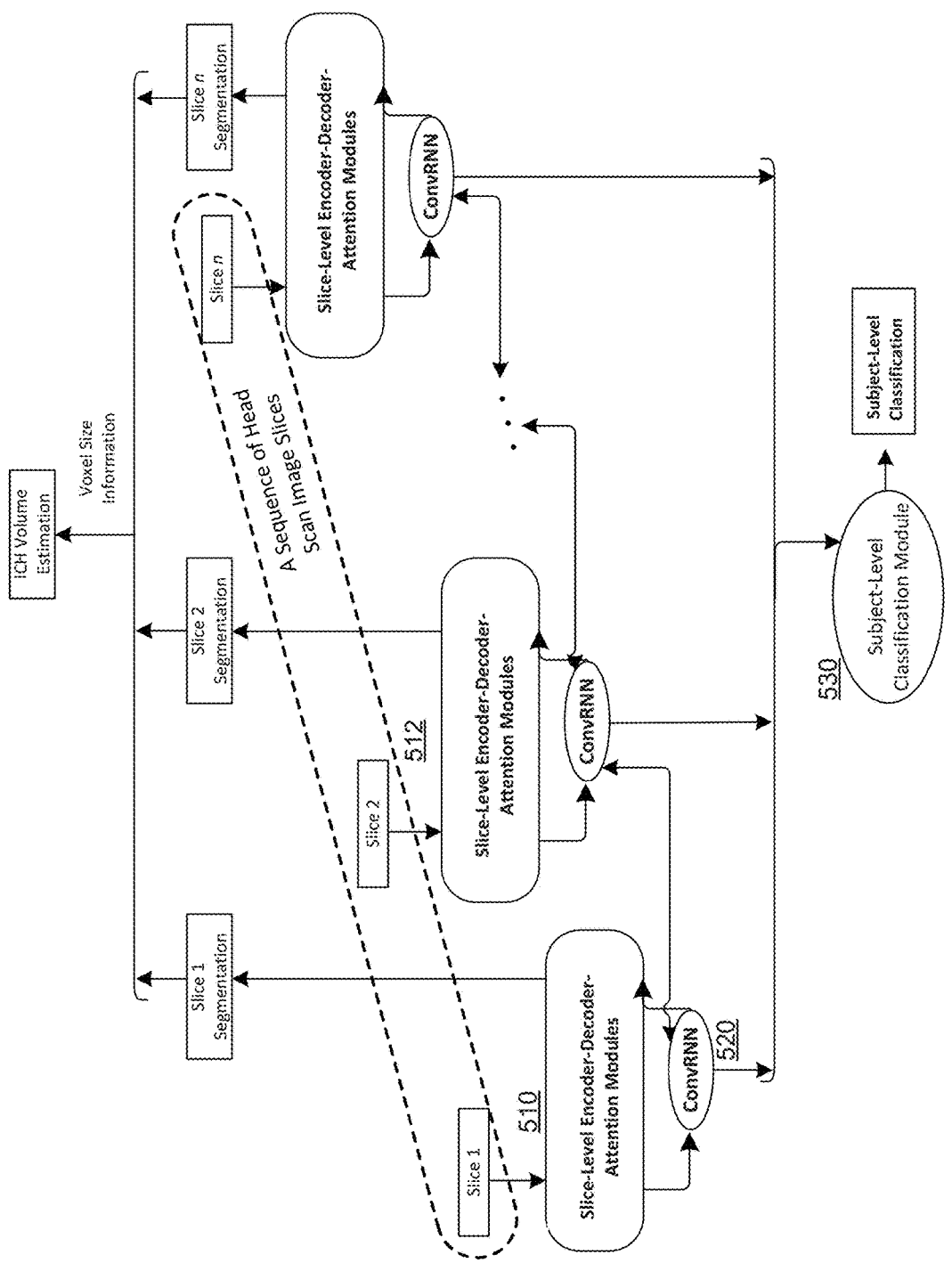
FIG. 5 is a flow diagram of an exemplary method for subject-level ICH detection, segmentation and volume estimation, according to embodiments of the disclosure.

In an exemplary embodiment, processor 308 may also process a sequence of image slices (e.g., slice 1, slice 2, . . . , slice n of a head scan) of a subject to generate subject-level ICH prediction and segmentation mark according to data diagram 500 as shown in FIG. 5. Each slice may be individually processed by the slice-level encoder-decoder-attention modules in parallel. For example, slice is processed by slice-level encoder-decoder-attention modules 510 and slice 2 is processed by slice-level encoder-decoder-attention modules 520. Certain intermediate information generated by the slice-level encoder-decoder-attention modules of every two adjacent image slices may be fed to the ConvRNNs. For example, information of slice 1 (generated by modules 510) and information of slice 2 (generated by modules 520) are fed into ConvRNN 520. The ConvRNNs then extract contextual information between the adjacent slices, which will be used to enhance the features maps. In some embodiments, feature maps of each image slice generated using the ConvRNNs may be fused to obtain the subject-level feature maps using fusion operations (e.g., average pooling, max pooling, or a combination of the two). For example, the subject-level feature maps from some or all ConvRNNs are then fed into a subject-level classification module 530 to obtain a subject-level ICH prediction. In some embodiments, decoder and attention modules may be used to generate segmentation masks for image slices of the subject in parallel. Voxel size information extracted from the segmentation masks may be used to estimate the bleeding volume. An exemplary image classification and segmentation process will be described in connection with FIG. 8.

In some embodiments, processor 308 may use only some modules of learning model 200 to perform either only ICH detection (e.g., using encoder module 202, ConvRNN module 206, and classification module 208) or only segmentation (e.g., using encoder module 202, ConvRNN module 206, and decoder module 204).

Consistent with the present disclosure, model training device 102 can have same or similar structures as image processing device 103. In some embodiments, model training device 102 includes a processor, among other components, configured to jointly train modules in the end-to-end multi-task learning model. An exemplary network training process will be described in connection with FIG. 7.

Figure 7:
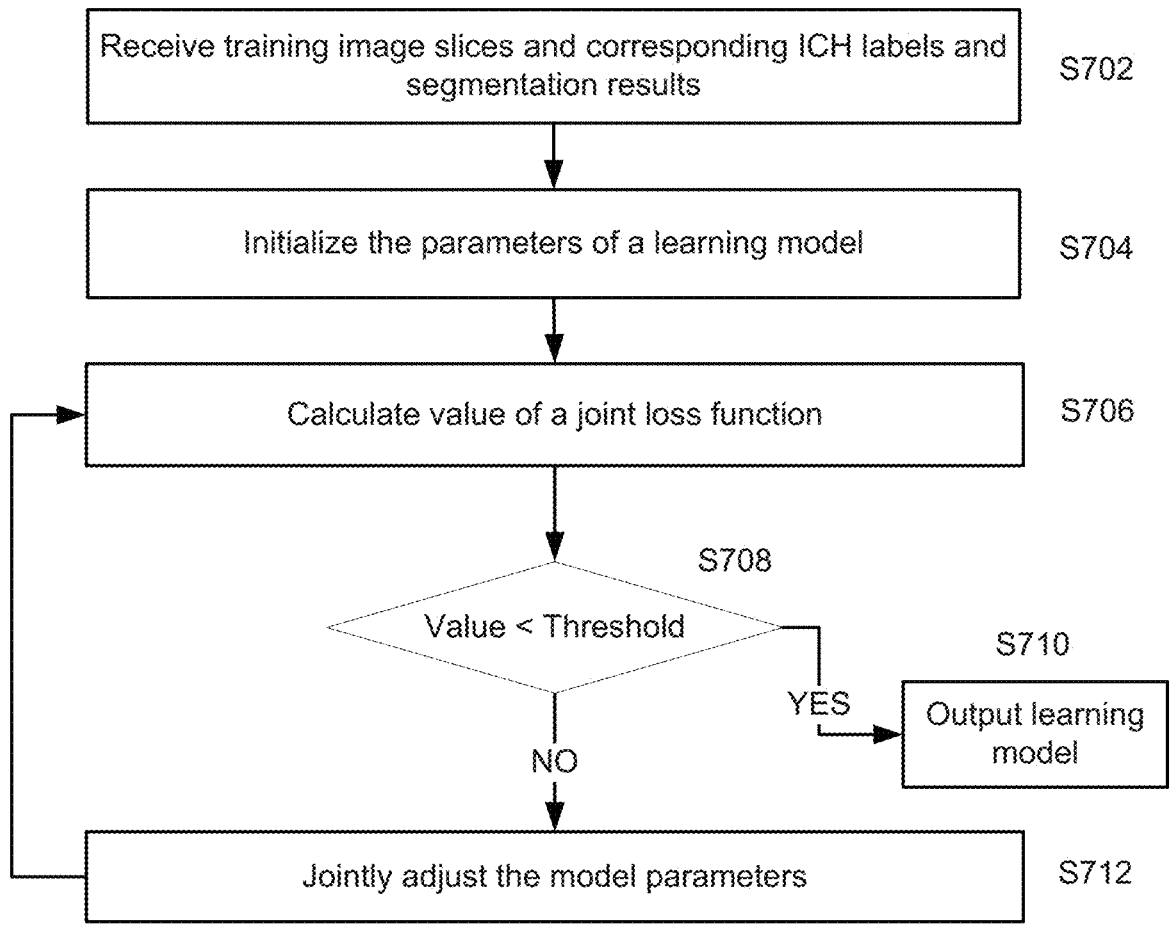
FIG. 7 is a flowchart of an exemplary method for training an end-to-end multi-task learning model, according to embodiments of the disclosure.

FIG. 7 is a flowchart of an exemplary method 700 for training an end-to-end multi-task learning model, according to embodiments of the disclosure. For example, method 700 may be implemented by model training device 102 in FIG. 1. However, method 700 is not limited to that exemplary embodiment. Method 700 may include steps S702-S712 as described below. It is to be appreciated that some of the steps may be optional to perform the disclosure provided herein. Further, some of the steps may be performed simultaneously, or in a different order than shown in FIG. 7.

In step S702, model training device 102 may communicate with training database 101 to receive one or more sets of training data. Each set of training data may include a sequence of image slices of a subject (e.g., a patient's head scan images) and its corresponding ground truth ICH labels (optionally also ICH subtype labels) and segmentation masks that provides the segmentation result to each image slice.

In step 704, model training device 102 may initialize the parameters of a learning model. Training the learning model is a process of determining one or more parameters of the learning model. In some embodiments, the learning model may include encoder module 202, decoder module 204, ConvRNN module 206, classification module 208, and attention module 210. Consistent with the present disclosure, model training device 102 jointly trains the various modules in the learning model, using the training data from training database 101. That is, the set of parameters of the modules are trained together. The parameters may be initially set to certain values. The initial values may be predetermined, selected by an operator, or decided by model training device 102 based on prior experience of similar image slices. For example, parameters of a learning model previously trained for head scan image slices of patient A may be used as initial values for the parameters of the learning model being trained for head scan image slices of patient B.

In step S706, model training device 102 may calculate the value of a joint loss function. In some embodiments, the joint loss function may be a weighted combination of a slice-level classification loss, a subject-level classification loss, a segmentation loss, and an ICH volume loss. In some embodiments, binary cross entropy (BCE) loss may be used to represent the slice-level classification loss and the subject-level classification loss. In some embodiments, soft dice loss or cross entropy may be used to represent the segmentation loss. In some embodiments, quadratic loss may be used to represent the ICH volume loss.

In step S708, the calculated value may be compared with a predetermined threshold. The predetermined threshold is also known as the stopping criteria for iterative methods. The smaller it is, the more optimal the parameters, but the longer it takes (i.e., more iterations) for the computation to converge. Therefore, the threshold may be selected to balance the accuracy of the prediction and the computational cost.

If the value is below the predetermined threshold (step S708: Yes), the method is considered as have converged, and the joint loss function is minimized. In step S710, model training device 102 outputs the learning model with the optimized sets of parameters and method 700 concludes. Otherwise (step S708: No), model training device 102 may further adjust the sets of parameters jointly in step S712. In some embodiments, a stochastic gradient descent related method with backpropagation may be used. For example, the parameters may be adjusted with a gradient $\nabla \mathcal{L}$ of the loss function $\mathcal{L}$ with respect to all parameters over image slices sampled from the training dataset. Method 700 may return to step S706 to calculate value of the loss function based on outputs obtained from the learning model with the adjusted sets of parameters. Each pass of steps S706-S712 is considered as one iteration. Method 700 iterates until the value of the loss function is reduced to below the predetermined threshold (step S708).

Figure 8:
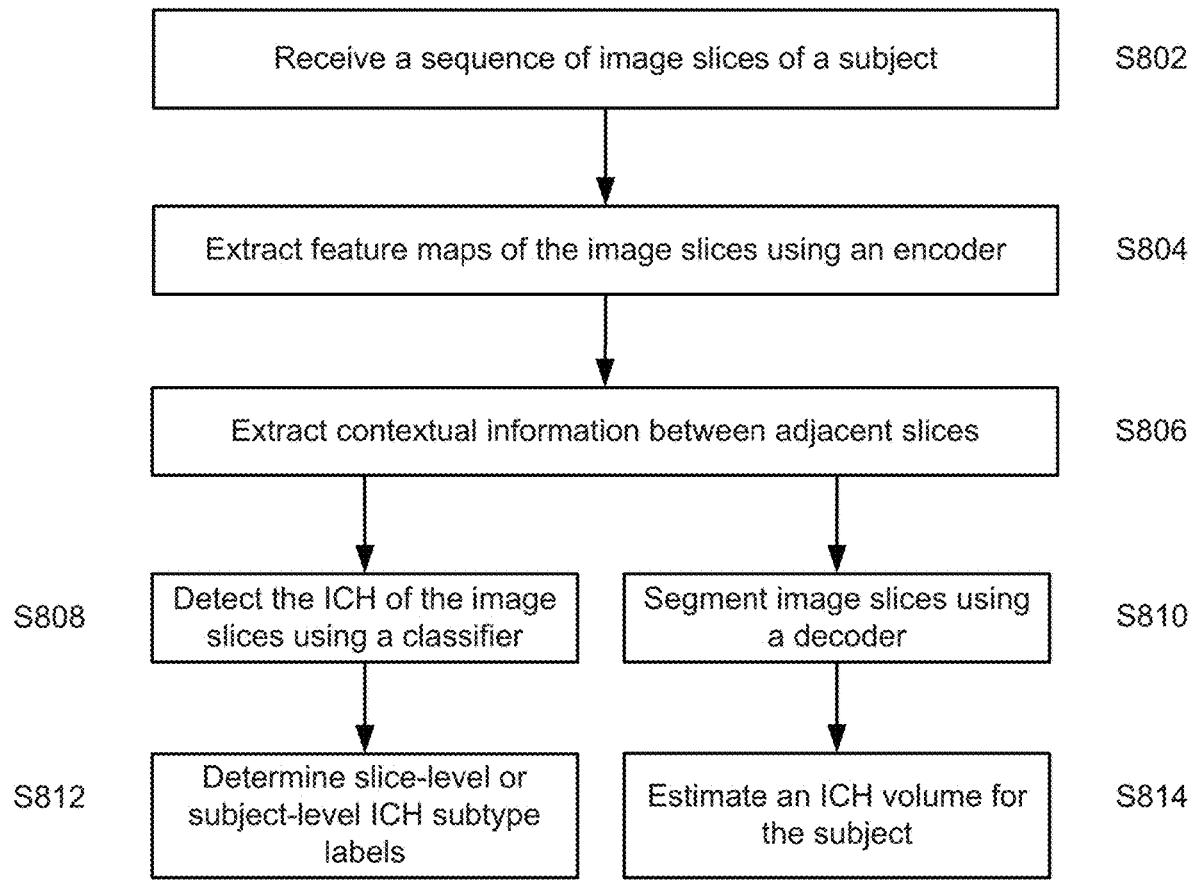
FIG. 8 is a flowchart of an exemplary method for ICH detection and segmentation using an end-to-end multi-task learning model, according to embodiments of the disclosure.

FIG. 8 is a flowchart of an exemplary method 800 for ICH detection and segmentation using an end-to-end multi-task learning model, according to embodiments of the disclosure. For example, method 800 may be implemented by image processing device 103 in FIG. 1 using learning model 200 in FIG. 2. However, method 800 is not limited to that exemplary embodiment. Method 800 may include steps S802-S814 as described below. It is to be appreciated that some of the steps may be optional to perform the disclosure provided herein. Further, some of the steps may be performed simultaneously, or in a different order than shown in FIG. 8.

In step S802, image processing device 103 receives a sequence of image slices, e.g., from head scan image database 104. The image slices may capture an ICH. Image processing device 103 may additionally receive a learning model, e.g., end-to-end multi-task learning model 200. In some embodiments, the learning model may be trained using method 700.

In step S804, image processing device 103 extracts feature maps from the image slices. In some embodiments, the individual slices may be processed independently and in parallel. For example, the feature maps may be extracted at different granularities by encoder module 202 of learning model 200. In step S806, image processing device 103 extracts contextual information between every two adjacent image slices among the sequence of image slices. For example, feature maps of adjacent image slices (e.g., slice 1 and slice 2 in data diagram 500) are fed into ConvRNN module (e.g., ConvRNN 520 of data diagram 500). In some embodiments, the spatial relationship between two feature maps are extracted.

In step S808, image processing device 103 may perform ICH prediction on each image slice. Image processing device 103 can also perform a subject-level ICH prediction. For example, all slice-level feature maps and contextual information between image slices are used to determine if the subject has an ICH. For example, slice-level classification module 406 is used to detect ICH for each image slice and subject-level classification module 530 is used to detect ICH for the subject.

In step S810, image processing device 103 can further perform ICH subtype prediction on each image slice if ground truth subtype labels are used to train the learning model. Image processing device 103 can additionally perform a subject-level ICH subtype prediction. For example, all slice-level feature maps and contextual information between image slices are used to determine the ICH subtype of the subject.

In step S812, image processing device 103 may segment the image slices using a decoder module, e.g., decoder model 204. In some embodiments, the decoder module fuses all slice-level feature maps and contextual information between image slices to produce a segmentation mask for each image slice. In some embodiments, image processing device 103 may segment the image slices using parallel computing. In some embodiments, the decoder may produce a probability map indicating the probability each pixel in the image slice belongs to the bleeding region. Based on the probability map, image processing device 103 may then perform a thresholding to obtain a segmentation mask.

In step S814, image processing device 103 may estimate the bleeding volume of the subject. For example, the segmentation masks generated in step S812 are used to obtain the voxel size information and calculate the bleeding volume.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for detecting an intracerebral hemorrhage (ICH), comprising:
a communication interface configured to receive a sequence of image slices and an end-to-end multi-task learning model, the sequence of image slices being head scan images of a subject acquired by an image acquisition device, the end-to-end multi-task learning model comprising an encoder, a bi-directional Convolutional Recurrent Neural Network (ConvRNN), a decoder, and a classifier; and
at least one processor, configured to:
extract feature maps from each image slice using the encoder;
capture contextual information between adjacent image slices using the bi-directional ConvRNN; and
detect the ICH of the subject using the classifier based on the extracted feature maps of the image slices and the contextual information or segment each image slice using the decoder to obtain an ICH region based on the extracted feature maps of the image slice.

2. The system of claim 1, wherein the at least one processor is further configured to detect the ICH of the subject using the classifier and to segment each image slice using the decoder in parallel.

3. The system of claim 2, wherein the at least one processor is further configured to estimate an ICH volume for the subject based on the ICH regions in the image slices.

4. The system of claim 1, wherein to detect the ICH, the at least one processor is further configured to determine:
a slice-level ICH label for each image slice; or
a subject-level ICH label for the subject.

5. The system of claim 1, wherein to detect the ICH, the at least one processor is further configured to determine:
a slice-level ICH subtype label for each image slice; or
a subject-level ICH subtype label for the subject.

6. The system of claim 1, wherein the contextual information is determined based on a spatial relationship between every two adjacent image slices among the sequence of image slices.

7. The system of claim 1, wherein the end-to-end multi-task learning model is a Fully Convolutional Network (FCN), wherein the encoder is a Convolutional Neural Network (CNN).

8. The system of claim 1, wherein the bi-directional ConvRNN is a bi-directional Convolutional Long Short-Term Memory (ConvLSTM) or a bi-directional Convolutional Gated Recurrent Unit (ConvGRU).

9. The system of claim 1, wherein the end-to-end multi-task learning model is trained using a joint loss function including a weight combination of a slice-level classification loss, a subject-level classification loss, a segmentation loss, and an ICH volume loss.

10. The system of claim 1, wherein the end-to-end multi-task learning model further includes an attention module, and the at least one processor is further configured to enhance the extracted feature maps using the attention module.

11. A method for detecting an intracerebral hemorrhage (ICH), comprising:
receiving a sequence of image slices and an end-to-end multi-task learning model, the sequence of image slices being head scan images of a subject acquired by an image acquisition device, the end-to-end multi-task learning model comprising an encoder, a bi-directional Convolutional Recurrent Neural Network (ConvRNN), a decoder, and a classifier;
extracting, by at least one processor, feature maps from each image slice using the encoder;
capturing, by the at least one processor, contextual information between adjacent image slices using the bi-directional ConvRNN; and
detecting, by the at least one processor, the ICH of the subject using the classifier based on the extracted feature maps of the image slices and the contextual information or segmenting, by the at least one processor, each image slice using the decoder to obtain an ICH region based on the extracted feature maps of the image slice.

12. The method of claim 11, wherein detecting the ICH of the subject using the classifier and segmenting each image slice using the decoder are performed in parallel.

13. The method of claim 12, further comprising estimating an ICH volume for the subject based on the ICH regions in the image slices.

14. The method of claim 11, wherein detecting the ICH further comprises determining:
 a slice-level ICH label for each image slice; or
 a subject-level ICH label for the subject.

15. The method of claim 11, wherein detecting the ICH further comprises determining:
 a slice-level ICH subtype label for each image slice; or
 a subject-level ICH subtype label for the subject.

16. The method of claim 11, wherein the contextual information is determined based on a spatial relationship between every two adjacent image slices among the sequence of image slices.

17. The method of claim 11, wherein the end-to-end multi-task learning model is a Fully Convolutional Network (FCN), wherein the encoder is a Convolutional Neural Network (CNN).

18. The method of claim 11, wherein the bi-directional ConvRNN is a bi-directional Convolutional Long Short-Term Memory (ConvLSTM) or a bi-directional Convolutional Gated Recurrent Unit (ConvGRU).

19. The method of claim 11, wherein the end-to-end multi-task learning model is trained using a joint loss function including a weight combination of a slice-level classification loss, a subject-level classification loss, a segmentation loss, and an ICH volume loss.

20. A non-transitory computer-readable medium having a computer program stored thereon, wherein the computer program, when executed by at least one processor, performs a method for detecting an intracerebral hemorrhage (ICH), the method comprising:
 receiving a sequence of image slices and an end-to-end multi-task learning model, the sequence of image slices being head scan images of a subject acquired by an image acquisition device, the end-to-end multi-task learning model comprising an encoder, a bi-directional Convolutional Recurrent Neural Network (ConvRNN), a decoder, and a classifier;
 extracting feature maps from each image slice using the encoder;
 capturing contextual information between adjacent image slices using the bi-directional ConvRNN; and
 detecting the ICH of the subject using the classifier based on the extracted feature maps of the image slices and the contextual information or segmenting each image slice using the decoder to obtain an ICH region based on the extracted feature maps of the image slice.

* * * * *